United States Patent [19]

Toy et al.

[11] Patent Number: 5,618,290
[45] Date of Patent: Apr. 8, 1997

[54] ENDOSCOPIC SUTURE PASSER AND METHOD

[75] Inventors: Frederick K. Toy; Roy T. Smoot, Jr.; Robert H. LaPrad, all of Seaford, Del.

[73] Assignee: W.L. Gore & Associates, Inc., Newark, Del.

[21] Appl. No.: 377,762

[22] Filed: Jan. 24, 1995

Related U.S. Application Data

[63] Continuation-in-part of Ser. No. 14,349, Oct. 19, 1993, Pat. No. Des. 368,776.

[51] Int. Cl.$^6$ ............................................. A61B 17/04
[52] U.S. Cl. ........................... 606/139; 606/144; 606/145
[58] Field of Search .................................. 606/144, 145, 606/146, 148, 151, 232, 139

[56] References Cited

U.S. PATENT DOCUMENTS

| | | | |
|---|---|---|---|
| 2,268,755 | 1/1942 | Li | 128/326 |
| 3,088,454 | 5/1963 | Shute | 128/2 |
| 4,235,238 | 11/1980 | Ogia et al. | 606/145 |
| 4,660,570 | 4/1987 | Dombrowski | 128/765 |
| 4,928,669 | 5/1990 | Sullivan | 128/4 |
| 5,100,415 | 3/1992 | Hayhurst | 606/139 |
| 5,181,919 | 1/1993 | Bergman et al. | 606/144 |
| 5,281,237 | 1/1994 | Gimpelson | 606/144 |
| 5,290,297 | 3/1994 | Phillips | 606/144 |
| 5,304,187 | 4/1994 | Green et al. | 606/151 |
| 5,320,629 | 6/1994 | Noda et al. | 606/139 |
| 5,480,405 | 1/1996 | Yoon | 606/139 |

*Primary Examiner*—Gary Jackson
*Attorney, Agent, or Firm*—Dann, Dorfman, Herrell and Skillman; Henry H. Skillman

[57] ABSTRACT

An endoscopic suturing device is provided for manipulating a suture to form a stitch through a tissue within a body cavity. The suturing device comprises a needle with a shaft, a pointed head located at the distal end of the needle shaft, a hook formed proximally to the pointed head, and a latch for opening and closing the hook. The latch is biased to the open position. A tubular sheath is provided which is concentric with the needle shaft, the needle shaft being frictionally slidable within the tubular shaft. The suture is clamped by the device by inserting the suture into the hook and sliding the tubular sheath over the latch, thereby closing the hook. The suture can then be released by sliding the tubular sheath to uncover the latch, thereby opening the hook.

25 Claims, 7 Drawing Sheets

ENDOSCOPIC SUTURE PASSER AND METHOD

RELATED APPLICATION

This application is a continuation-in-part of our application Ser. No. 29/014,349, filed Oct. 19, 1993, now U.S. Pat. No. Des. 368,776.

FIELD OF THE INVENTION

The present invention relates to an endoscopic suturing device and a method of performing endoscopic surgical procedures using the device wherein tissue within a body cavity is secured using sutures.

BACKGROUND OF THE INVENTION

Endoscopic surgical techniques have been used successfully to perform a variety of surgical procedures including vagotomies, appendectomies, laparotomies, gall-bladder removals, lysis of adhesions from scar tissue, and hernia repairs, in addition to many other operations.

The use of endoscopic surgical procedures can provide benefits over conventional surgical techniques to both the surgeon and the patient. The time required to perform endoscopic surgery is often significantly less than the time required to perform the same operation using conventional surgical techniques. In addition, endoscopic procedures decrease the amount of pain and discomfort suffered by the patient while also decreasing the recovery time and the amount of scarring.

However, endoscopic surgical procedures are hampered because such procedures require the use of specialized tools in order to effectively work in an endoscopic surgical environment. Since only a small incision is made in the patient, the surgeon's access to the operating site is restricted. Therefore, new instruments are needed when working in an endoscopic environment.

Devices for endoscopically closing hernia defects have been developed and can be broadly classified as either stapling or suturing devices. Although sutures are cheaper and less likely to cause adverse reactions, current suturing devices suffer in that they do not securely clamp the suture and the suture is difficult to mount within the device. Furthermore, existing devices make it difficult to place the sutures in the operating site at the optimal locations for suture passing and tying. As a result, endoscopic suturing techniques generally require longer operating times than do stapling techniques.

U.S. Pat. No. 4,923,461 relates to a method for arthroscopic suturing of tissue within the body without requiring open surgery. The method involves penetrating the tissue to be sutured with a hollow needle and feeding the suture material through the hollow needle. The needle is then removed and the suture knotted. However, this method has the disadvantage of having to clamp onto the suture end and withdraw it from the body in order to knot the suture. In addition, this method cannot be used to provide a running seam. Further, the device necessary to perform such a procedure is bulky and, therefore, restrictive in use.

Accordingly, it would be highly desirable to have an endoscopic suturing device that is easy to use, easy to manipulate, and securely clamp the suture, and wherein the suture is easily mounted within the suture passer. In use, the suturing device should enable placement of the sutures at optimum locations in the operating site and desirably enable tying of the sutures subcutaneously.

SUMMARY OF THE INVENTION

In accordance with the present invention, an endoscopic suturing device is provided for suturing tissue within a body cavity during endoscopic surgical procedures. The device is easy to use, easy to manipulate, and securely clamps the suture. Additionally, the suture is easily mounted within the suturing device.

The device comprises a suture passer having a needle with a pointed head adapted to be inserted through the skin into the body cavity. A hook is provided proximally to the pointed head. A latch, which is spring-biased to the open position, is provided for opening and closing the hook. A tubular sheath is provided which is concentric with the needle, the needle being frictionally slidable within the tubular sheath, so that the hook is open when the latch is extended from the tubular sheath and the hook is closed when the latch is retracted within the tubular sheath.

The present invention also provides a method for utilizing the suture passer to manipulate a suture to form a stitch in a tissue within a body cavity. The suture is positioned with at least a first part of the suture on a first side of the tissue. The first part of the suture is then drawn through the tissue thereby positioning the first part of the suture on a second side of the tissue, leaving a second part of the suture on the first side. The first part of the suture is then drawn back through the tissue at a spaced location from the previous point of entry into the tissue. The first part of the suture is then united with the second part of the suture to close the stitch through the tissue.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE INVENTION

Figure 1:
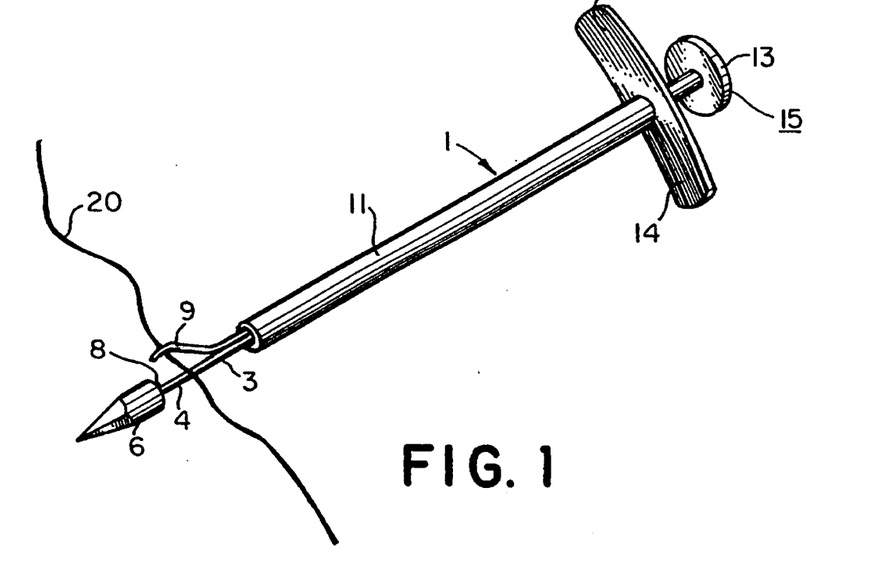
FIG. 1 is a perspective view of a first embodiment of a suture passer embodying the present invention for manipulating a suture to form a stitch in a tissue within a body cavity.
Figure 2:
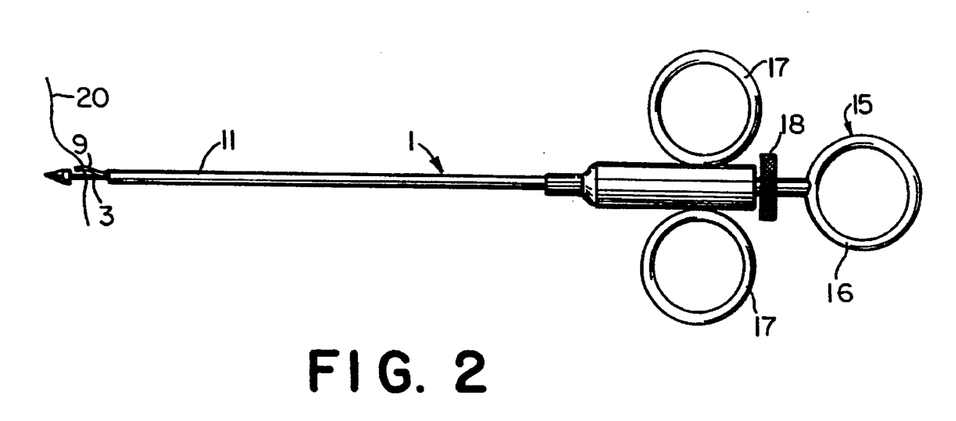
FIG. 2 is a front elevational view of a second and preferred embodiment of a suture passer embodying the present invention with the hook in the open position.
Figure 3:
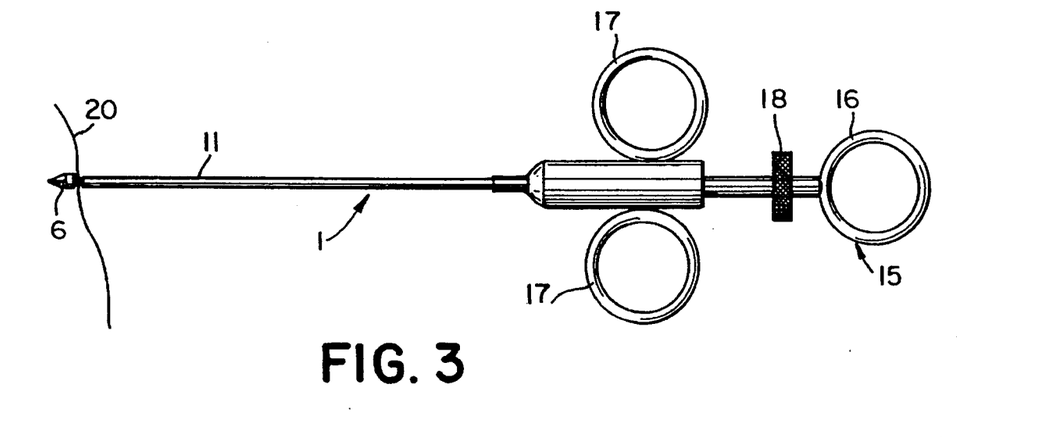
FIG. 3 is a front elevational view of the device in the closed position.
Figure 4:
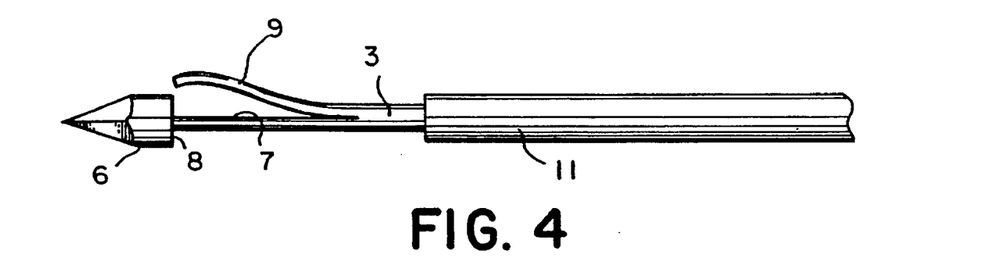
FIG. 4 is an enlarged fragmentary front elevational view of the distal end of the suturing device with the hook in the open position.
Figure 5:
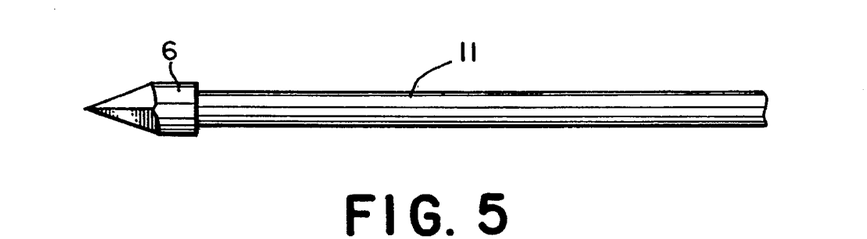
FIG. 5 is a view similar to FIG. 4 with the hook in the closed position.

FIGS. 1 through 3 show two forms of endoscopic suturing device, generally designated 1, for endoscopically suturing tissue within a body cavity. Each suturing device 1 comprises a needle shaft 3. An enlarged pointed head 6 is formed at the distal end 4 of the needle shaft 3. The underside of the pointed head 6 at its junction with the shaft 3 forms a shoulder which provides a hook 8. A latch 9, which is spring-biased to the open position, is provided for opening and closing the hook 8. A tubular sheath 11 surrounds and is concentric with the needle shaft 3 and is dimensioned so that the needle shaft 3 is frictionally slidable within the tubular sheath 11. The hook 8 can be opened by extending the needle shaft 3 to space its head 6 from the distal end of the tubular sheath 11 as shown in FIG. 2, and the hook 8 can be closed by retracting the needle shaft 3 to withdraw the latch 9 within the tubular sheath 11, causing the latch to close against the shaft. In this manner, a suture 20 can be selectively captured by or released from the suturing device 1. A handle 15 is provided at the proximal end of the suture passer 1.

The handle includes a grip on the shaft 3 and a cooperating grip on the sheath 11. In the embodiment of FIG. 1, the shaft grip is in the form of a plunger thumb rest 13, and the sheath grip is in the form of a pair of finger rests 14,14, similar to the grip portion of a hypodermic needle. In the embodiment of FIG. 2, the shaft grip comprises a thumb loop 16 and the sheath grip comprises finger loops 17 to extend the latch 9 relative the tubular sheath 11. Either embodiment of the handle 15 aids in manipulating the suturing device 1. In each embodiment, the sliding engagement of the shaft in the sheath not only permits relative axial displacement, but also affords relative rotational displacement of the shaft within the sheath. It is preferred to provide rotation of the shaft 3 within the sheath to vary the presentation of the hook and facilitate manipulation of the suture when it is engaged in the hook without having to rotate the sheath when it is placed into the body cavity. In the embodiment of FIG. 1, the thumb plunger 13 may be rotated to rotate the shaft 3 within the sheath, and in the embodiment of FIG. 2, a thumbwheel 18 is provided to serve as a rotator for the shaft 3. Rotation of the shaft 3 at the proximal end of the suture passer affords rotation of the hook 8 at the distal end of the suture passer.

In the present instance, the latch 9 comprises a flexible leaf which is formed integrally with the shaft by a longitudinal cut 7 extending from the head 6 a short distance towards the proximal end. The free end of the leaf 9 produced by the cut 7 is severed from the shaft 3 and is biased to a position in which it curves outwardly from the cut to provide a separation between the free end of the leaf 9 and the hook 8. In this position, the leaf opens the hook to allow capture of a suture between the leaf 9 and the body of the shaft 3. The flexibility of the leaf allows the free end of the leaf to close the hook, for example when the shaft 3 is withdrawn into the interior of the sheath 11. The hook 8, in the present instance, is formed at the junction of the cut 7 with the underside of the enlarged head 6.

It is noted that the needle shaft 3 is of lesser diameter than the head 6 so that a shoulder is formed at the underside of the head 6 at its junction with the shaft 3. As shown, the sheath 11 is tubular in form with an interior diameter adapted to frictionally and slidably receive the shaft 3 and an outer diameter which is slightly less than the outer diameter of the head 6. Thus, when the shaft 3 is withdrawn into the sheath 11, the sheath flexes the leaf 9 against the cut 7 and allows the distal end of the sheath 11 to engage against the shoulder formed at the underside of the head 6. If a suture is captured within the hook 8, the longitudinal displacement of the sheath relative to the head 8 not only captures the suture within the hook, but also clamps the suture between the end of the sheath 11 and the underside of the head 6. In accordance with the invention, the flexible leaf 9 is biased outwardly from the cut 7 so that the hook 8 is normally open.

Preferably, the needle shaft 3 is constructed from a spring material and is heat treated to provide a spring bias for the latch 9. In addition, the shaft 3, the pointed head 6, the hook 8, the latch 9 and the sheath 11 are preferably fabricated from heat-resistant material so as to withstand sterilizing temperatures without degradation of the spring bias or the frictional sliding of the shaft 3 within the sheath 11. Typically, the needle shaft 3, the pointed head 6, the hook 8, and the latch 9 are fabricated from a single piece of 174-PH grade stainless steel. The needle shaft 3 is about 6.96 in. (17.68 cm) long and about 0.041 in. (1.04 mm) in diameter. The pointed head 6 is about 0.5 in. (1.27 cm) long with a diameter of about 0.061 in. (1.549 mm) at its widest point. The underside of the head 6 and the flexible leaf 9 are formed by cutting the needle shaft 3 proximally to the pointed head 6 and perpendicularly to the centerline of the needle shaft 3 to a depth of about 0.002 in. (0.051 mm). A second cut, extending about 1 in. (2.54 cm), is made perpendicular to the first cut and parallel to the centerline of the needle shaft 3, thereby forming an L-shaped groove 7 described above. The latch 9 is then shaped by bending the leaf of material formed by the two cuts to provide an enlarged latch opening to facilitate the stitching operation. When heat treated, the leaf 9 is biased outwardly away from the head 6.

The tubular sheath 11 comprises an approximately 4 in. (10.16 cm) length of 316 stainless steel tubing with an inner diameter of about 0.047 in. (1.194 mm) and an outer diameter of about 0.058 in. (1.473 mm). These dimensions allow the tubular sheath 11 to frictionally slide over the needle shaft 3 and to permit the shaft 3 to frictionally rotate about its longitudinal axis within the sheath 11. Preferably, the outer diameter of the tubular sheath 11 is only slightly less than the diameter of the pointed head 6 at its widest point, thereby facilitating insertion and withdrawal of the suturing device 1 through the skin. In addition, the tubular wall of the sheath 11 is sufficiently thick to allow for opening and closing the latch 9 without significant distortion of the tubular wall of the sheath 11.

Figure 6:
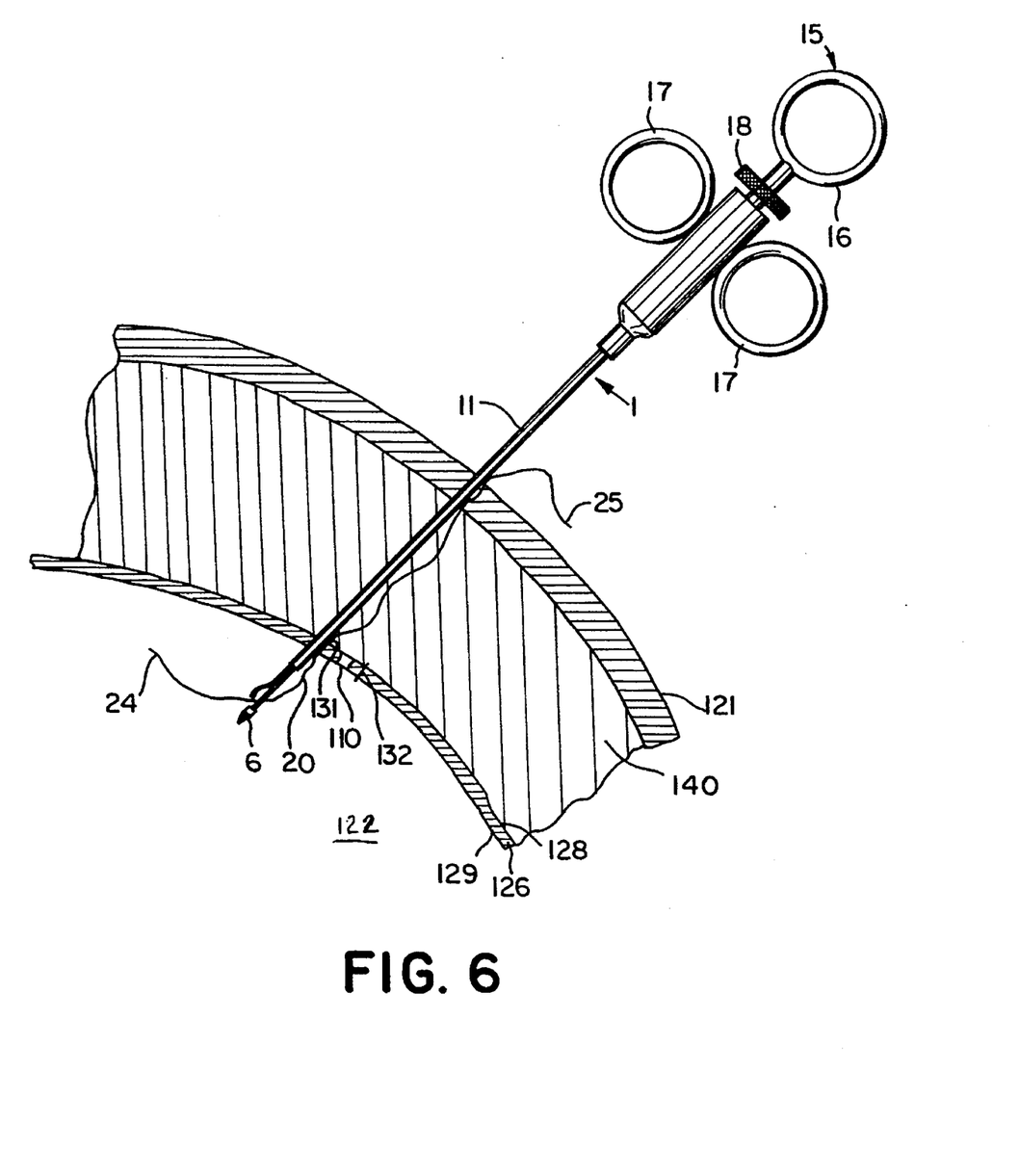
FIG. 6 is a sectional view through a body cavity showing an operating site with a suture passer in position for manipulating a suture to form a stitch in a tissue within the body cavity.

In operation, a method of manipulating a suture to form a stitch in a tissue within a body cavity is described and shown in FIG. 6. FIG. 6 illustrates diagrammatically a surgical site where a layer of tissue 126 has been cut, leaving an incision 110 in the tissue layer 126. As shown, the tissue is within the body cavity 122 and is separated from the outer skin 121 by a subcutaneous fatty layer 140. The operating site may be viewed by an optical viewer positioned within the body cavity 122 so as to facilitate the surgeon's closure of the incision 110. The incision is closed by using a suture passer 1. To apply the stitches using a suture 20, the leading part 24 of the suture 20 is clamped into the hook 8 extracorporeally by displacing the sheath 11 against the underside of the head 6 of the suturing device 1. The skin 121 enclosing the body cavity 122 is then penetrated with the pointed head 6 of the suturing device 1. The pointed head 6 is advanced through a fatty subcutaneous layer 140 and is then advanced from the outer side 128 through the tissue 126 at a puncture point 131 adjacent the incision 110 to position the leading part 24 of the suture 20 on the inner second side 129 of the tissue 126. The needle shaft is advanced through the sheath 11 as shown in FIG. 6 to open the latch 9 to release the suture 20 from the suturing device 1. The pointed head 6 is then withdrawn back through the tissue 126, at the puncture point 131 leaving the first part 24 of the suture 20 on the second or inner side 129 of the tissue 126. After withdrawal of the pointed head 6 through the tissue 126, the pointed head 6 is translated along the first outer side 128 of tissue 126 across the incision 110 through the subcutaneous layer 140. The pointed head 6 is then advanced through the tissue 126 at a second puncture point 132 (see FIG. 7) at a spaced location on the other side of the incision from the puncture point 131. When the distal end of the suture passer 1 is in the cavity 122, the hook 8 of the suture passer 1 is manipulated to capture the free end 24 of the suture 20 and the latch 9 is operated to clamp onto the body of the suture 20 at a position adjacent the leading part 24. The pointed head 6 is then withdrawn from the tissue 126 at the puncture point 132 bringing with it the leading end 24 of the suture 20. A conventional knot could be used to tie or otherwise unite the leading part 24 of the suture 20 to a second part 25 of the suture 20 at the first side 128 of the tissue so that the suture 20 is tightened against the tissue 126 to provide a stitch closing the incision 110.

The two parts 24 and 25 may be knotted together extracorporeally. The suturing device 1 may then be translated to other locations to provide additional stitches either by angling the suturing device 1 or by withdrawing the suturing device 1 from the skin 121 and re-penetrating the skin 121 at a new location.

Figure 7:
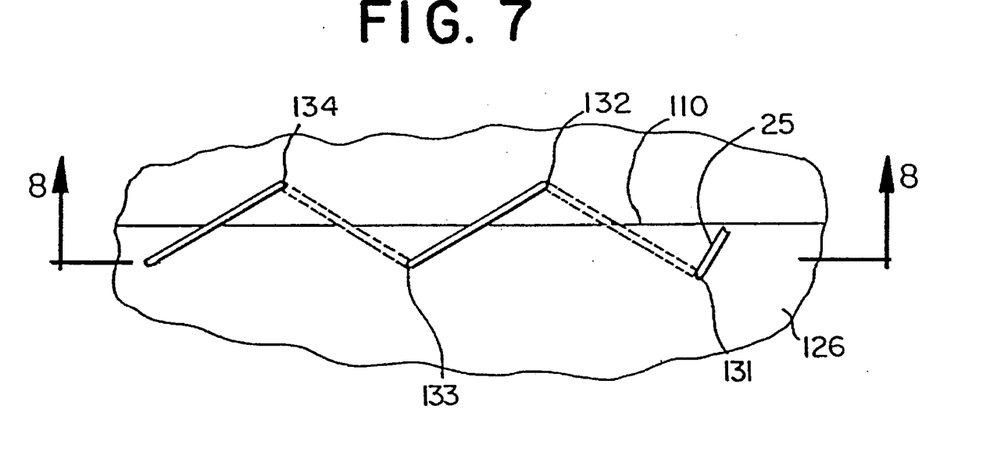
FIG. 7 is an enlarged fragmentary view of an operating site showing an incision having a running seam for closing the incision.
Figure 8:
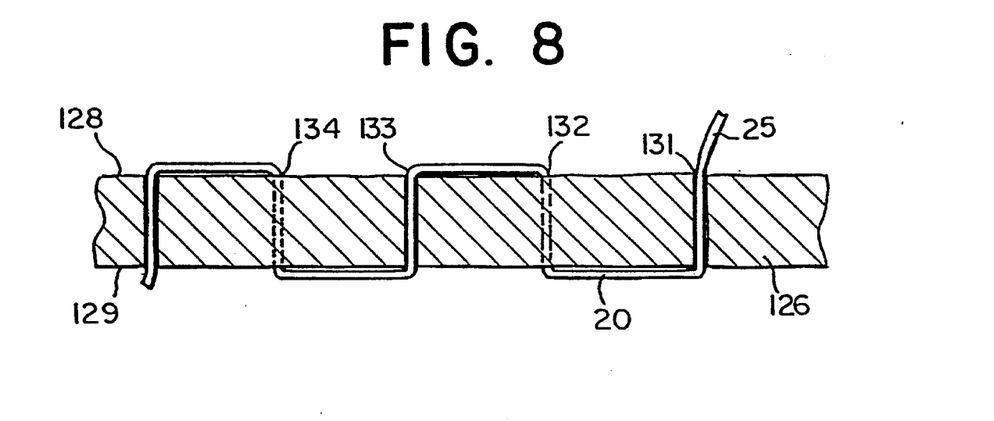
FIG. 8 is a sectional view taken on the line 8—8 of FIG. 7 showing a running mattress stitch seam formed by the use of a suture passer made in accordance with the present invention.

FIGS. 7 and 8 illustrate that the suture passer 1 can be used to provide a running seam along the length of the incision 110, as opposed to individual stitches. To provide a seam, as shown in FIGS. 7 and 8, the leading part 24 of the suture 20 remains captured by the suturing device 1 instead of being tied or united to the second part 25 of the suture 20. The pointed head 6 of the suturing device 1 is advanced through the subcutaneous layer 140 to a third puncture point 133 to draw the leading part 24 of the suture 20 to the second side 129 of the tissue 126. The latch 9 of the suturing device 1 is operated to release the body of the suture 20 from the suturing device 1. The pointed head 6 is then withdrawn from the tissue 126 through the puncture point 133 while leaving the first part 24 of the suture 20 on the second side 129 of the tissue 126. After withdrawal of the pointed head 6 through the tissue 126, the pointed head 6 is translated along the first side 128. The pointed head 6 is advanced through the tissue 126 at another puncture point 134 at a spaced location from the puncture point 133. The latch 9 is operated to clamp onto the leading part 24 of the suture 20, and the pointed head 6 is then withdrawn from the tissue 126, bringing with it the first part 24 of the suture 20. This procedure is repeated until a running seam has been provided along the length of the incision 110. A conventional knot can then be used to tie or otherwise unite the first part 24 of the suture 20 to the second part 25 of the suture 20 so that the suture 20 is tightened against the tissue 126 thereby closing the incision. Preferably, the two parts 24 and 25 are knotted together extracorporeally.

Figure 9:
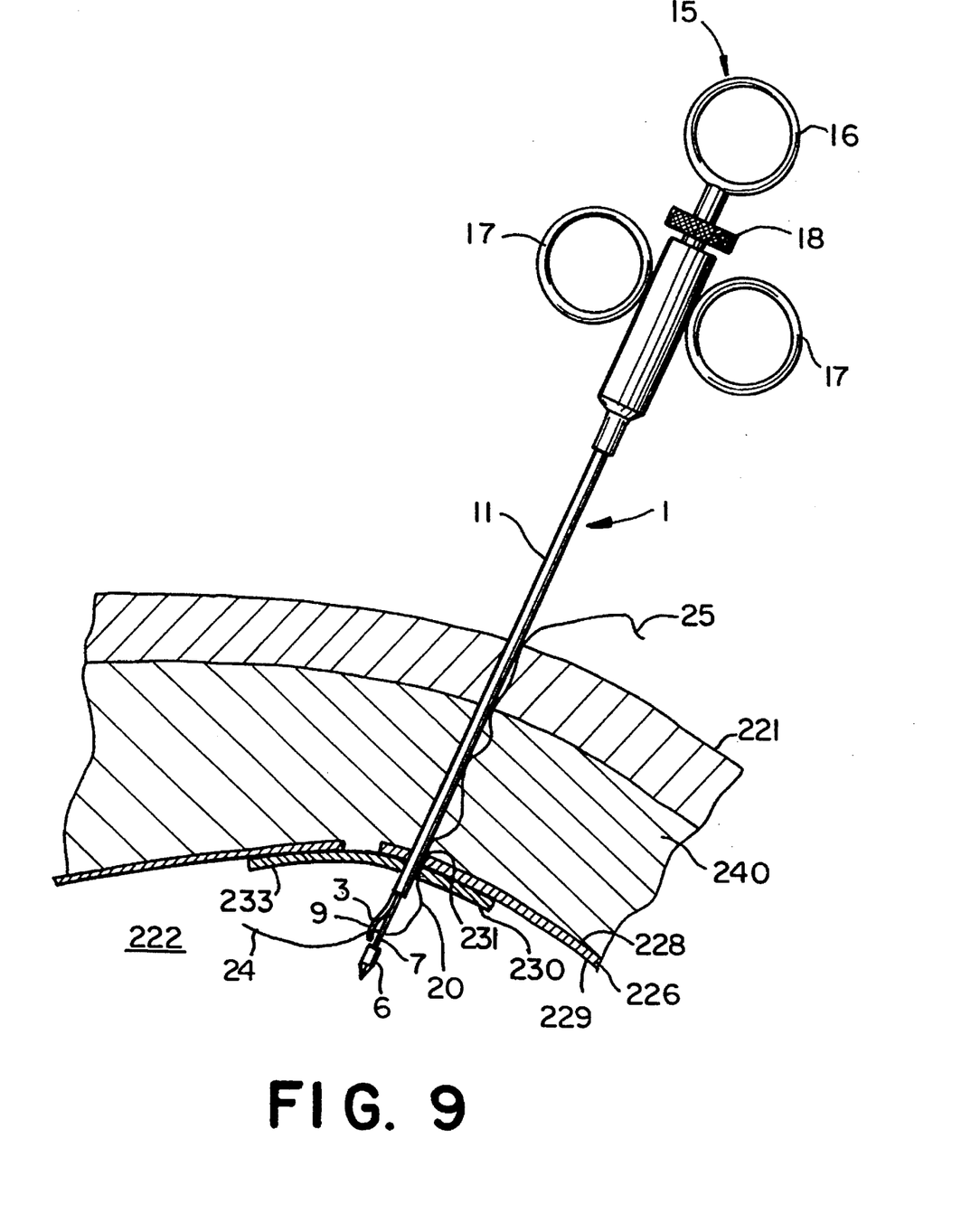
FIG. 9 is a view similar to FIG. 6 showing the method of securing a patch to one surface of a tissue within a body cavity by manipulating a suture to form a stitch.

A method of securing a patch to one surface of a tissue within a body cavity by manipulating a suture to form a stitch is described and shown in FIG. 9. A suture 20 is positioned with at least the first part 24 of the suture 20 being captured by a suturing device 1. A skin 221 enclosing a body cavity 222 is punctured with a pointed head 6 of the suturing device 1. The pointed head 6 is advanced through a fatty subcutaneous layer 240. A patch 230 is positioned over the tissue 226. The pointed head 6 is then advanced through the tissue 226 and the patch 230 at a puncture point 231 to position the first part 24 of the suture 20 on an underside 233 of the patch 230. The latch 9 is then operated to release the body of the suture 20 from the suturing device. The pointed head 6 is then withdrawn from the tissue 226 and the patch 230 while maintaining the first end 24 of the suture 20 on the second side 229 of the tissue 226 and the underside 233 of the patch 230. After withdrawal of the pointed head 6 through the tissue 226 and the patch 230, the pointed head 6 is translated along the first side 228 of the tissue 226 through the subcutaneous layer 240. The pointed head 6 is advanced through the tissue 226 and the patch 230 at a second puncture point (not shown in FIG. 9) at a spaced location from the puncture point 231. The hook 8 of the suture passer 1 is manipulated to capture the free part 24 of the suture 20, and the latch 9 is again operated to clamp the suture 20. The pointed head 6 is then withdrawn from the tissue 226 and the patch 230 bringing with it the first part 24 of the suture 20. A conventional knot may be used to tie or otherwise unite the first part 24 of the suture 20 to the second part 25 of the suture 20 to provide a stitch so that the suture 20 is tightened against the tissue 226 thereby anchoring the patch 230. Preferably, the two parts 24 and 25 are knotted together extracorporeally.

The suture 20 does not have to be positioned with the first part 24 of the suture 20 being captured by the suturing device 1 prior to penetration of the pointed head 6 through the skin. Instead, the first part 24 of the suture 20 can be independently positioned on the one side of the tissue and/or patch to be sutured. The suturing device 1 can then penetrate the skin and capture the first part 24 of the suture 20 after penetration of the tissue and/or the patch by the pointed head 6. The suturing procedure may then follow the steps outlined above.

Alternatively, multiple suture parts can be attached to the patch prior to positioning the patch over the tissue. The parts of the suture 20 may be attached to the patch 230 extracorporeally. The patch is then inserted into the cavity and spread across the damaged area of the tissue. After the device penetrates the cavity, the latch 9 is operated to clamp onto the first part of the suture 20, and that part is drawn out and released. The pointed head 6 is then advanced through the tissue 226 at a second puncture point to capture the next part of the suture 20 and is withdrawn to release the next part. The parts may be knotted together to anchor the patch in place. The same procedure may be used with all of the suture parts which are attached to the patch, thereby anchoring the patch to the tissue. Preferably, the various parts are knotted together extracorporeally.

Figure 10:
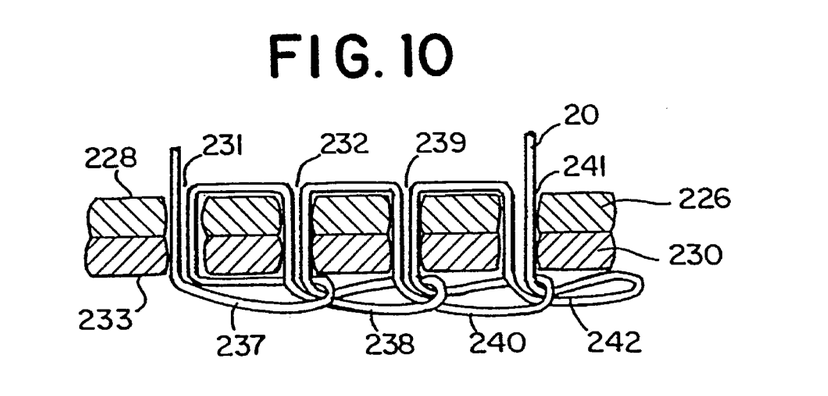
FIG. 10 is a fragmentary cross-sectional view of the operating site in FIG. 9 showing a patch secured in place by a running seam comprising chain stitches.

To provide a chain stitch, as shown in FIG. 10, a suture 20 is positioned with at least a medial part of the suture 20 being captured by the suturing device 1. A patch 230 is positioned over the tissue 226. The pointed head 6 of the suturing device 1 is advanced through the tissue 226 and the patch 230 at a puncture point 231 to position the first part 24 of the suture 20 on the underside 233 of the patch 230. A sufficient length of suturing material is pulled through the patch 230 and the tissue 226 to provide a loop 237 of suturing material on the underside 233 of the patch 230 when the pointed head 6 is withdrawn from the tissue 226 and the patch 230. The pointed head 6 is then withdrawn from the tissue 226 and the patch 230 while maintaining the loop 237 of suturing material on the underside 233 of the patch 230. After withdrawal of the pointed head 6 through the tissue 226 and the patch 230, the pointed head 6 is translated along the upper side 228 of the tissue 226. The pointed head 6 is advanced through the patch 230 and the tissue 226 at another puncture point 232 at a spaced location from the puncture point 231. The pointed head 6 is made to pass through the loop 237 of suturing material. A sufficient length of suturing material is again pulled through the patch 230 and the tissue 226 to provide a loop 238 of suturing material on the underside 233 when the pointed head 6 is withdrawn from the tissue 226 and the patch 230. The pointed head 6 is then withdrawn from the tissue 226 and the patch 230 while maintaining the loop 238 on the underside 233. This procedure is repeated at puncture points 239 and 241 to form loops 240 and 242. Loop 242 is the end of the running seam provided substantially around the perimeter of the patch 230. After loop 242 is formed, the suturing device is operated to release the suture part forming the loop 242, and the pointed head 6 is manipulated to capture the suture part in the bight of the loop 242 and to draw it back through the puncture point 241. The suture part in the bight of the loop 242 may be severed extracorporeally and tied to the leading part of the suture 20 so that the suture 20 is tightened against the tissue 226 thereby anchoring the patch 230. Preferably, the two parts are knotted together extracorporeally. It should be noted that in forming the chain stitch, the suture parts should be captured in the hook, but it is not necessary or desirable to clamp the suture part in the hook. To accomplish this end, the sheath 11 and shaft 3 are manipulated to leave sufficient clearance between the distal end of the sheath and the shoulder defined by the underside of the head to allow longitudinal passage of the suture through the closed hook without allowing the suture to escape from capture.

Figure 11:
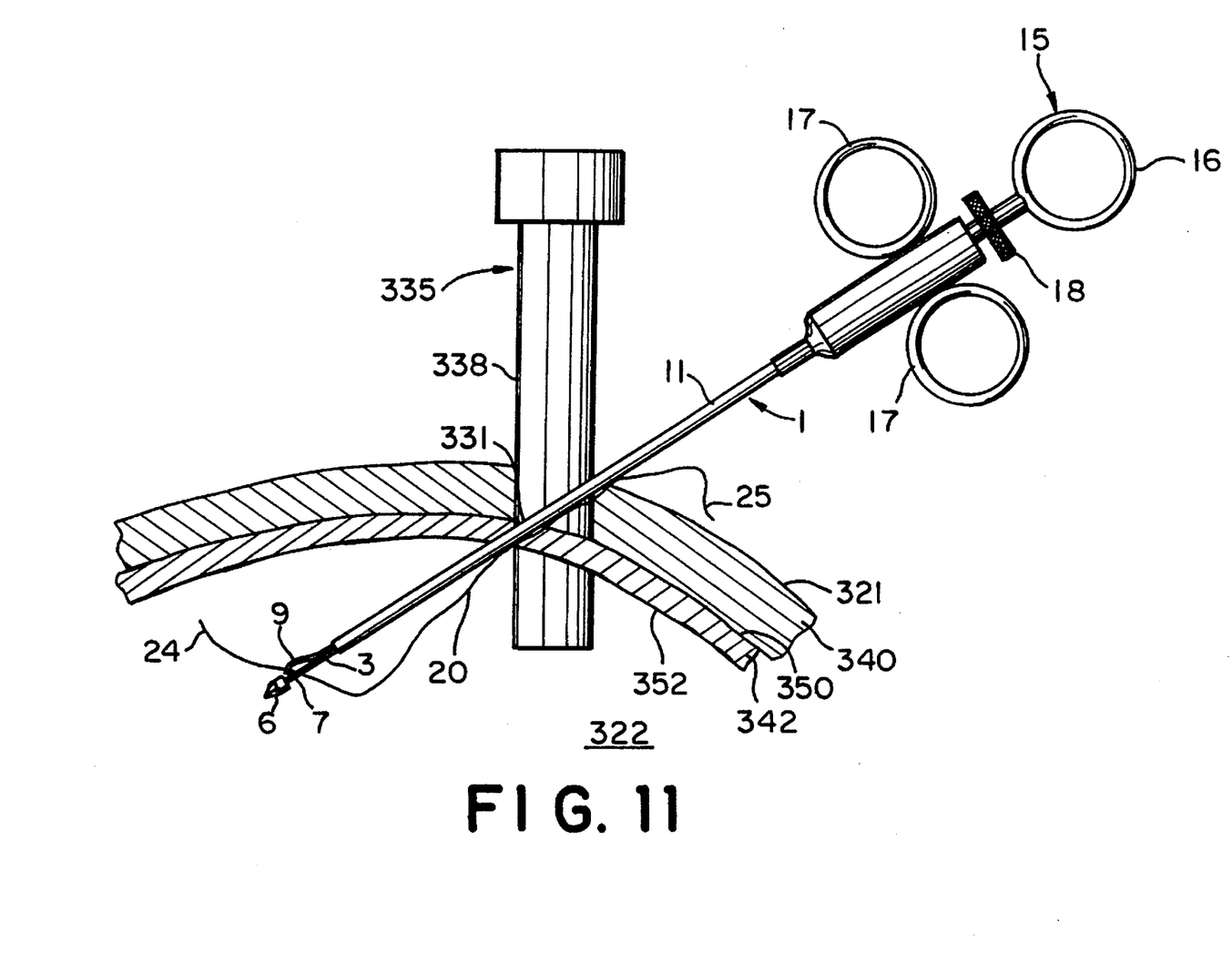
FIG. 11 is a fragmentary sectional view of an operating site showing a method of closing an incision, made in a tissue for the insertion of a trocar tube into a body cavity, by manipulating a suture to form a stitch with a suture passer of FIG. 2.

A method of sealing an incision, made for the insertion of a trocar tube into a body cavity, by manipulating a suture to form a stitch, is described and shown in FIG. 11. While the trocar tube 335 is still inserted in an incision, a suture 20 is positioned with at least a first part 24 of the suture 20 being captured by a suturing device 1. A pointed head 6 of the suturing device 1 is advanced through a fascia 350, a muscle 342, and a peritoneum 352 at a puncture point 331 positioned near an outer surface 338 of a trocar tube 335 to capture the first end 24 of the suture 20 within a body cavity 322. A latch 9 is operated to release the body of the suture 20 from the suturing device 1. The pointed head 6 is then withdrawn back through the peritoneum 352, the muscle 342, and the fascia 350 while maintaining the first part 24 of the suture 20 within the body cavity 322. The pointed head 6 is then translated along the fascia 350. The pointed head 6 is advanced through the fascia 350, the muscle 342, and the peritoneum 352 at a second puncture point (not shown in FIG. 11) at a location near the outer surface 338 of the trocar tube 335 which is spaced from the previous puncture point 331 and on the opposite side of the trocar tube 335. The latch 9 is operated to clamp onto the body of the suture 20 at a spaced position from the first part 24. The pointed head 6 and the first part 24 of the suture 20 are withdrawn from the peritoneum 352, the muscle 342, and the fascia 350. The suture 20 can then be tightened around the trocar tube 335 to close the tissue around the trocar tube 335.

The trocar tube 335 can be further secured in place by providing additional stitches. With latch 9 clamping onto the body of suture 20, the pointed head 6 is passed through the fascia 350, the muscle 342, and the peritoneum 352 at a third puncture point spaced from the second puncture point and near the outer surface 338 of the trocar tube 335, thereby positioning the first part 24 of the suture 20 within the body cavity 322. The latch 9 is operated to release the body of the suture 20 from the suturing device 1. The pointed head 6 is withdrawn through the peritoneum 352, the muscle 342, and the fascia 350 at the third puncture point. The pointed head 6 is then translated along the fascia 350. The pointed head is then passed through the fascia 350, the muscle 342, and the peritoneum 352 at a fourth puncture point spaced from the third puncture point and near the outer surface 338 of the trocar 335. The latch 9 is operated to clamp onto the body of the suture 20 at a spaced position from the first part 24. The pointed head 6 and the first part 24 of the suture 20 are withdrawn from the peritoneum 352, the muscle 342 and the fascia 350. Preferably, the locations of the puncture points are selected to form a figure-eight pattern. The suture 20 can then be tightened around the trocar tube 335 to close the tissue around the trocar tube 335.

When the trocar tube 335 is to be removed, the suture 20 is loosened and the trocar tube 335 is then removed from the incision. A conventional knot may be used to tie or otherwise unite the first part 24 of the suture 20 to a second part 25 of the suture 20 to provide a stitch thereby simultaneously sealing the three internal layers of the incision. Preferably, the two ends 24 and 25 are knotted together extracorporeally.

Figure 12:
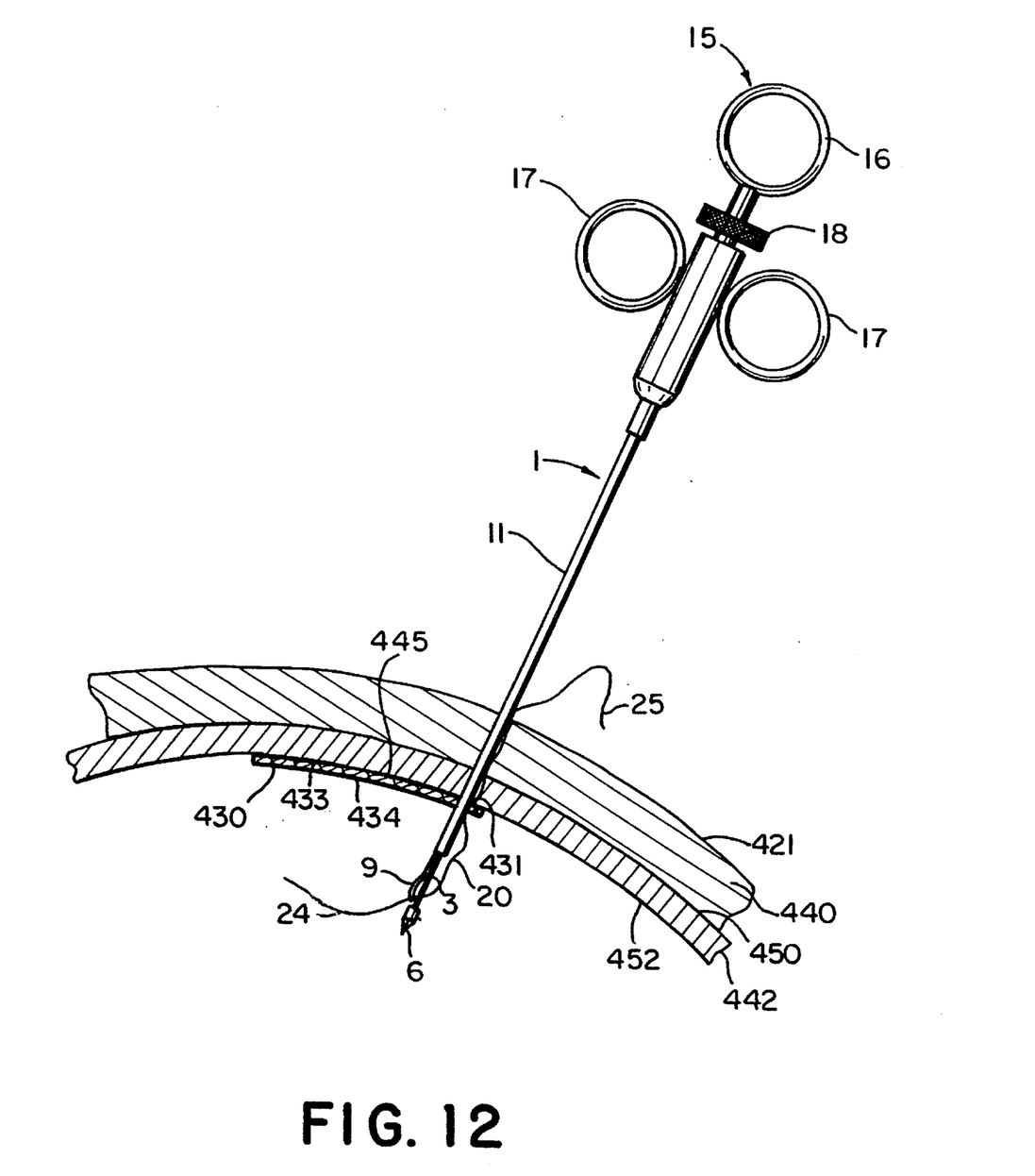
FIG. 12 is a sectional view of an operating site depicting a method of securing an internal patch to cover a hernia defect by using a suture passer of FIG. 2 for manipulating a suture to form stitches.

A method of securing a patch to cover a hernia defect by manipulating a suture to form a stitch is described and shown in FIG. 12. A suture 20 is positioned with at least the leading part 24 of the suture 20 being captured by a suturing device 1. A skin 421 is punctured with a pointed head 6 of the suturing device 1. The pointed head 6 is advanced through a fatty subcutaneous layer 440. A patch 430 is spread over the damaged area containing the hernia defect 445, with a first side 433 of patch 430 in contact with a peritoneum 452 and covering the hernia defect 445. The pointed head 6 is then advanced through a fascia 450, a muscle 442, a peritoneum 452, and the patch 430 at a puncture point 431 to position the first part 24 of suture 20 on a second side 434 of the patch 430. A latch 9 is operated to release the body of the suture 20 from the suturing device 1. The pointed head 6 is then withdrawn from the patch 430, the peritoneum 452, the muscle 442, and the fascia 450 while leaving the first part 24 of the suture 20 on the second side 434 of the patch 430. After withdrawal of the pointed head 6 through the patch 430, the peritoneum 452, the muscle 442, and the fascia 450, the pointed head 6 is translated along the fascia 450 through the subcutaneous layer 440. The pointed head 6 is advanced through the fascia 450, the muscle 442, the peritoneum 452, and the patch 430 at a second puncture point (not shown) at a spaced location from the previous puncture point 431. The latch 9 is then operated to clamp onto the body of the suture 20 at a position spaced from the leading part 24. The pointed head 6 is then withdrawn from the patch 430, the peritoneum 452, the muscle 442, and the fascia 450 bringing with it the first part 24 of the suture 20. A conventional knot may be used to unite the first part 24 of the suture 20 to a second part 25 of the suture 20 so that the suture 20 is tightened against the muscle 442 to provide a stitch thereby anchoring the patch 430. Preferably, the two parts 24 and 25 are knotted together extracorporeally.

The suturing device of the present invention is designed to be used in a variety of surgical procedures including, but not limited to, vagotomies, appendectomies, laparotomies, gall-bladder removals, lysis of adhesions from scar tissue, and hernia repairs.

Suitable patch materials include any one of a number of nonabsorbable synthetic materials. These materials include polypropylene mesh, i.e., Marlex® (C. R. Bard, Inc., Murray Hill, N.J.) or Prolene® (Ethicon, Inc., Summerville, N.J.); polyester mesh, i.e., Mersilene® (Ethicon, Inc., Summerville, N.J.); expanded polytetrafluoroethylene or ePTFE. i.e., GORE-TEX® Soft Tissue Patch (W. L. Gore & Associates, Inc., Flagstaff, Ariz.) or GORE-TEX DualMesh™ Biomaterial (W. L. Gore & Associates, Inc., Flagstaff, Ariz.); or multifilament, knitted polypropylene mesh, i.e., Surgipro® (United States Surgical Corporation, Norwalk, Conn.); monofilament, knitted polypropylene mesh (i.e., Trelex™ Natural Mesh (Meadox Medicals, Inc., Oakland, N.J.).

Conventional suture materials are suitable for use in the suturing device of the present invention. Preferably, 2-0 nonabsorbable sutures are used.

EXAMPLES

Example 1

The suturing device of the present invention can be used to repair a hernia defect of the abdominal cavity. The procedure is performed under general anesthesia. The patient is given antibiotic prophylaxis, and the bladder is decompressed with a Foley catheter; the stomach is decompressed with a nasogastric tube. The patient is supine in the Trendelenburg position, and the television monitors are positioned at the patient's feet. A skin incision is made at the superior edge of the umbilicus, and a Veress needle is used to insufflate the abdomen with carbon dioxide for visualization of the peritoneal cavity. A 10/11 mm trocar is inserted into the peritoneal cavity via the umbilical incision, through which a 0-degree laparoscope is introduced. The abdominal cavity is then explored and the hernia defect confirmed. Two additional 10/11 mm trocars are inserted under direct vision. These trocars are placed at the level of the umbilicus along the anterior axillary lines.

If a hernia sac is present, the contents are reduced into the peritoneal cavity. In the case of large, direct hernias (such as sliding hernias), the sac is reduced by grasping the bowel or bladder fat with an atraumatic Babcock clamp and retracting it cephalad. The peritoneal reflection between the bowel and the hernia sac is easily identified and incised with endoscopic scissors, delivering the bowel back into the peritoneal cavity. The demarcation between the bladder and the hernia sac is not as obvious. To avoid inadvertently entering the bladder, dissection is begun on the anterior abdominal wall component of the medial umbilical ligament and continued inferiorly, incising only the peritoneum and teasing bluntly all bladder and perivesicle fat from the medial portion of the hernia sac. Dissection can also be started lateral to the defect at the level where the vas deferens crosses Cooper's ligament. The peritoneum is incised and the fatty areolar tissue is teased away bluntly, exposing Cooper's ligament. This blunt dissection is carried medially up to the pubic tubercle. These two maneuvers safely reduce the bladder into the peritoneal cavity, clearing the medial edge of the hernia defect for patch fixation. The sac is left in situ with no ligation of the internal ring.

When there is no sliding component on the medial edge of the defect, the medial umbilical ligament is incised laterally and reflected medially with endoscopic scissors. Dissection inferiorly and laterally exposes the pubic tubercle and Cooper's ligament. The dissection is carried laterally along Cooper's ligament up to the vas deferens, which courses over the external iliac vein at this level. Any redundant, floppy medial umbilical ligament is stapled medially to the anterior abdominal wall to prevent it from obstructing the surgeon's view.

A 0.04 in. (1 mm) thick 3.94 in. (10 cm)×5.90 in. (15 cm) Gore-Tex ePTFE Soft Tissue Patch or a Gore-Tex Dual Mesh Biomaterial (W. L. Gore & Associates, Inc., Flagstaff, Ariz.) is cut to 3.15 in. (8 cm)×4.72 in. (12 cm) in size and tailored inferiorly to conform with the oblique Cooper's ligament and iliopubic tract. The edge to be stapled to Cooper's ligament is highlighted with a sterile marker for easy orientation. At all four corners, 2-0 nonabsorbable sutures are attached, leaving approximately six inch (15.2 cm) strands. The patch is then attached to a two-pronged Endo-Patch Spreader using 2-0 nonabsorbable sutures. The medial corner of the patch (at the pubic tubercle) is attached to the short prong. This facilitates introduction of the patch into the peritoneal cavity and spreading and positioning of the inferomedial edge of the patch over the pubic tubercle and Cooper's ligament. The Endo-Patch Spreader is inserted through the contralateral 11 mm trocar and the patch is introduced. The Endopath® Endoscopic Multi-feed stapler (EMS) (Ethicon Endo-Surgery, Inc., Cincinnati, Ohio) is inserted through the ipsilateral 11 mm trocar. Several staples are placed, securing the patch to the pubic tubercle and Cooper's ligament up to the external iliac vein. The sutures attaching the patch to the spreader are then cut, and the Endo-Patch Spreader removed. The inferior lateral corner is grasped and positioned over the iliopubic tract and fixed with staples. The iliopubic tract is easy to identify without any dissection. Anterior abdominal wall counteraction is applied just above the inguinal ligament; this counteraction can be seen laparoscopically and palpated with the stapler head. The stapler head is then rolled inferiorly, just below the palpable fingers. This is the iliopubic tract from the laparoscopic perspective. To avoid injury to the femoral, genitofemoral, and/or lateral femoral cutaneous nerves, it is paramount not to staple dorsal to the iliopubic tract.

Using the endoscopic suturing device of the present invention, the sutures previously placed at each corner of the patch are secured. To do this, the location of the corners is identified on the skin surface using bimanual palpation or by passing a spinal needle for localization, or both. A 0.079 in. (2 mm) nick is made in the skin with a size 11-blade scalpel. The endoscopic suturing device is passed through the abdominal wall, opened, and the sutures are placed in the endoscopic suturing device using a smooth grasper (a 0.197 in. (5 mm) needle holder works well) from the opposite trocar. The suture is then grasped and pulled out through the skin. After retrieving both strands, the suture is tied down easily to the fascia, pushing through the subcutaneous fat. This is done at all four corners. The Endopath EMS is introduced via the contralateral trocar, and the patch is stapled anteriorly, medially and laterally to the endoabdominal fascia. Good fascial fixation of the staples anteriorly and laterally is facilitated by anterior abdominal wall counteraction. This provides secure and reliable fixation of the patch to the fascial structures, covering the indirect, direct, and femoral hernia spaces.

Additional sutures are placed wherever it is felt necessary, depending on the size and type of hernia. For the additional sutures, the location is identified and a nick is made in the skin. The 2-0 nonabsorbable suture is grasped with the endoscopic suturing device and passed through the abdominal wall and ePTFE patch. The suture is released and grasped with a smooth grasper. The endoscopic suturing device is then passed through the same skin incision but at a slightly different angle. The suture is then passed to the endoscopic suturing device, grasped, and pulled through the skin. By changing the angle slightly, the suture passes through the fascia, muscle, and ePTFE patch at a slightly different location. The suture is tied down to the fascia in a mattress stitch that incorporates the patch and all myofascial layers of the abdominal wall.

To prevent the occurrence of bowel obstructions from a Richter's hernia via a trocar site, trocar sites greater than 0.197 in. (5 mm) should be closed using the endoscopic suturing device of the present invention. While the abdomen is still insufflated and all the trocars are in place, a suture is grasped in the endoscopic suturing device and passed through the same skin incision adjacent to the trocar. The suture thereby passes through the fascia, the muscle, and the peritoneum. The suture is released intraabdominally and grasped with a blunt grasper. The endoscopic suturing device is removed and reinserted adjacent to the trocar on the opposite side. The suture is passed to the endoscopic suturing device, grasped, and pulled out through the skin. All of the sutures are placed under direct vision, leaving the strands long enough to tie later. The pneumoperitoneum is released, and the trocars are removed; the sutures are tied, closing all three of the interior layers at each trocar site. The skin is closed with 4-0 Vicryl® suture (Ethicon, Inc., Summerville, N.J.), subcuticular sutures, and steri-strips.

Example 2

The suturing device of the present invention can be used to repair ventral hernias. The procedure is performed under general anesthesia. The patient is given antibiotic prophylaxis, and the bladder is decompressed with a Foley catheter; the stomach is decompressed with a nasogastric tube. An alternative puncture site is chosen away from the hernia defect and any abdominal incisions. A skin incision is made and a Veress needle is inserted or an open technique is utilized and the abdomen is insufflated with carbon dioxide for visualization of the peritoneal cavity. A 30° laparoscope is introduced through the same incision. The abdominal cavity is explored, and the hernia defect and adhesions are identified. Under direct visualization, additional 11 mm trocars are inserted as far lateral as possible under direct vision. Enterolysis is performed utilizing an Endo-Babcock and/or Endo-Retractor to provide exposure and counteraction on the hernia contents and adhesions, which are lysed with endoscopic shears. All of the contents of the hernia sac are reduced into the peritoneal cavity. The hernia sac is left in situ.

Additional 11 mm trocars are introduced on the opposite side laterally under direct vision. The number and position of trocars placements must be individualized. Direct vision and palpation allow identification of the edges of the hernia defect. The edges are then drawn on the abdominal wall and a 0.039 in. (1 mm) thick ePTFE Soft Tissue Patch or Gore-Tex DualMesh Biomaterial is measured to overlap the defect by at least 1.18 in. (3 cm) in all directions and cut to the appropriate size. 2-0 nonabsorbable sutures are placed and tied at all four corners and the sutures are left approximately 6 inches (15.2 cm) long. The patch is then attached to a two-prong Endo-patch Spreader for introduction into the abdominal cavity. An 0.433 in. (11 mm) patch spreader can be used for patches as large as 3.94 in. (10 cm)×5.90 in. (15 cm). Larger patches require an 0.709 in. (18 mm) patch spreader, which is passed through an 0.709 in. (18 mm) trocar. The patch is then rolled up into the cannula of the patch spreader.

The patch is introduced and spread out in the peritoneal cavity. Each corner is identified intraabdominally by passing a spinal needle through the abdominal wall at the corners. Small skin incisions are made approximately 0.079 in. (2 mm) in size with a size 11-blade scalpel. The endoscopic suturing device is then passed through the abdominal wall and the sutures from the corner are grasped, pulled through, and tied, securing the corner of the patch. This is done at all four corners, holding the patch up against the anterior abdominal wall. The patch is then further secured circumferentially with 2-0 nonabsorbable sutures approximately every 1.97 in. (5 cm). The gaps between the sutures are further secured by stapling the patch to the transversalis fascia using an Endopath EMS from whichever trocar is convenient. The security of the patch is verified. No drains are used except for extremely large hernias. The trocar sites are closed with 2-0 sutures placed with the suturing device before removing the trocars as described above in Example 1. The trocars are removed and the sutures tied, closing the trocar defects. The skin is closed with 4-0 Vicryl, subcuticular sutures and steri-strips.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

We claim:

1. A suturing device comprising:

a needle having a shaft with a proximal and a distal end;

a pointed head at the distal end of said needle shaft;

a suture-receiving hook formed proximally to said pointed head, said head being larger than said shaft to provide a shoulder intermediate said shaft and said head, said shaft and shoulder forming said hook;

a latch displaceable between open and closed positions for opening and closing said hook, said latch being spring-biased to the open position; and means operable from the proximal end for operating said latch.

2. The device as recited in claim 1 wherein the means for operating said latch comprises a tubular sheath concentric with said needle shaft and extending between said proximal end and said latch, said needle shaft being frictionally slidable within said tubular sheath, said latch being displaced by said spring bias to open said hook when said needle shaft is extended relative to said tubular sheath and said latch being displaced by said sheath to close said hook when said needle shaft is retracted relative to said tubular sheath.

3. The device as recited in claim 2 further comprising a handle having one grip connected to said needle shaft at its proximal end and a second grip connected to the sheath at its proximal end for extending and retracting said hook relative to the distal end of said tubular sheath.

4. The device as recited in claim 3 further comprising a rotator attached to said shaft at its proximal end for rotating the shaft of said suturing device within said sheath, and rotating said hook at the distal end of the device.

5. The device as recited in claim 3 wherein said one grip comprises a thumb rest and said second grip comprises a pair of finger rests.

6. The device as recited in claim 3 wherein said one grip comprises a thumb loop and said second grip comprises a pair of finger loops.

7. The device as recited in claim 1 wherein the means for operating said latch comprises a tubular sheath concentric with said needle shaft and extending between said proximal end and said hook, and having an outer dimension at its distal end not substantially larger than said head, said needle shaft being frictionally slidable within said tubular sheath, said latch being displaced by said spring bias to open said hook when said needle shaft is extended relative to said tubular sheath and said latch being displaced by said sheath to close said hook when said needle shaft is retracted relative to said tubular sheath.

8. The device as recited in claim 7 further comprising a handle having one grip connected to said needle shaft at its proximal end and a second grip connected to the sheath at its proximal end for extending and retracting said hook relative to the distal end of said tubular sheath.

9. The device as recited in claim 8 further comprising a rotator attached to said shaft at its proximal end for rotating the shaft of said suturing device within said sheath, and rotating said hook at the distal end of the device.

10. The device as recited in claim 7 wherein said sheath at its distal end has an outer dimension slightly less than the outer dimension of said pointed head, and said distal end of said shaft abuts against said shoulder in said retracted position to clamp a suture received in the hook.

11. The device as recited in claim 1 wherein said shaft comprises spring material and said shaft has a longitudinal cut extending from said shoulder toward said proximal end providing a latch comprising a flexible leaf integral with said shaft and having a free end adjacent said shoulder, said leaf being normally biased toward an open position away from said shoulder opening said hook, and operable to be displaced against its bias to a closed position adjacent said shoulder closing said hook.

12. The device as recited in claim 11 wherein the means for operating said latch comprises a tubular sheath concentric with said needle shaft and extending between said proximal end and said latch, said needle shaft being frictionally slidable within said tubular sheath, said latch leaf being displaced by said spring bias to open said hook when said needle shaft is extended relative to said tubular sheath and said latch leaf being displaced by said sheath to close said hook when said needle shaft is retracted relative to said tubular sheath.

13. The device as recited in claim 12 further comprising a handle having one grip connected to said needle shaft at its proximal end and a second grip connected to the sheath at its proximal end for extending and retracting said needle shaft relative to the distal end of said tubular sheath.

14. The device as recited in claim 12 wherein said spring material comprises steel which is heat treated to provide a spring bias in the flexible leaf of said latch.

15. The device as recited in claim 14 wherein said spring material of said shaft, and the material of said head and said sheath are heat-resistant so as to withstand sterilizing temperatures without degradation of said spring bias or the frictional sliding of said shaft within said sheath.

16. A method of manipulating a suture in a tissue by releasing and capturing the suture within a body cavity, the suture having a first and a second part, comprising the steps of:

a. providing a suturing device having a needle shaft with a proximal end and a distal end, a hook and a latch at the distal end of said shaft, and a handle at the proximal end to open and close the hook with said latch, whereby steps of releasing and capturing the suture are effected by respectively opening and closing said hook with said latch;

b. positioning the suture with at least the first part of the suture on a first side of the tissue;

c. using the suturing device to engage and pass the first part of the suture through the tissue to the second side of the tissue at one point, leaving the second part of the suture on the first side of the tissue, thereby positioning the suture with the two parts of the suture on opposite sides of the tissue;

d. releasing the first part of the suture and withdrawing the suturing device through the tissue at said one point, and passing it through the tissue at a second point spaced from said one point; and e. opening the hook of the device, capturing the first part of the suture in the hook of said suturing device, closing the hook with the latch, and drawing the first part of the suture through the tissue from the second side to the first side at said second point, so as to enable forming a stitch through the tissue.

17. A method according to claim 16 wherein closing the hook of the suturing device also clamps the suture in the hook.

18. A method according to claim 16 including the step of slidably housing said needle shaft in a sheath for relative axial sliding displacement;

said opening and closing of the hook being accomplished by axial displacement of said shaft within said sheath.

19. A method according to claim 18, comprising the additional steps of:

f. using the suturing device to pass the first part of the suture through the tissue to the second side at a third point spaced from the second point;

g. releasing the first part of the suture and withdrawing the suturing device through the tissue at said third point, and passing it through the tissue at a fourth point spaced from said third point; and h. opening the hook of the device, capturing the first part of the suture with said suturing device, closing the hook with the latch, and drawing the first part of the suture through the tissue at said fourth point from the second side to the first side, so as to enable forming a running seam.

20. A method according to claim 18 for securing a patch to said second side of the tissue comprising the additional steps of:

spreading the patch over the tissue on its second side to overlie said first and second points; and passing said suturing device also through said patch when performing steps c, d and e, thereby to enable forming a stitch anchoring said patch to said tissue.

21. A method according to claim 16, comprising the additional steps of:

f. using the suturing device to pass the first part of the suture through the tissue to the second side at a third point spaced from the second point; and g. releasing the first part of the suture and withdrawing the suturing device through the tissue at said third point, and passing it through the tissue at a fourth point spaced from said third point; and h. capturing the first part of the suture with said suturing device and drawing it through the tissue at said fourth point from the second side to the first side, so as to enable forming a running seam.

22. A method according to claim 16 for securing a patch to said second side of the tissue comprising the additional steps of:

spreading the patch over the tissue on its second side to overlie said first and second points; and passing said suturing device also through said patch when performing steps c, d and e, thereby to enable forming a stitch anchoring said patch to said tissue.

23. A method of securing a patch to one side of a tissue within a body cavity, comprising the steps of:

positioning a patch having plurality of suture parts attached thereto within the body cavity;

spreading the patch over one surface of the tissue;

using a suturing device to penetrate the tissue at a first point, to capture a first of said suture parts while on the one side of said tissue, and to draw said suture part through the tissue at said first point to the other side of said tissue;

releasing the first part and passing the suturing device through the tissue at a second point spaced from the first point;

capturing a second suture part with said device and drawing it through the tissue at said second point to the other side of said tissue; and connecting said two suture parts at the other side of said tissue to secure said patch in place.

24. A method according to claim 23 wherein said capturing step is effected by hooking and clamping the suture part with said suturing device.

25. A suturing device comprising:

a needle having a shaft with a proximal and a distal end;

a pointed head at the distal end of said needle shaft;

a suture-receiving hook formed proximally to said pointed head;

a latch displaceable between open and closed positions for opening and closing said hook, said latch being spring-biased to the open position;

a tubular sheath concentric with said needle shaft and extending between said proximal end and said latch, said needle shaft being frictionally slidable within said tubular sheath, said latch being displaced by said spring bias to open said hook when said needle shaft is extended relative to said tubular sheath and said latch being displaced by said sheath to close said hook when said needle shaft is retracted relative to said tubular sheath; and a rotator attached to said shaft at its proximal end for rotating the shaft of said suturing device within said sheath, and rotating said hook at the distal end of the device.

* * * * *